United States Patent
Day

(10) Patent No.: US 11,701,332 B2
(45) Date of Patent: Jul. 18, 2023

(54) METHODS AND COMPOSITIONS FOR TREATING FEMALE SEXUAL INTEREST AND AROUSAL DISORDER

(71) Applicant: Bryce Nicholas Day, Townsville (AU)

(72) Inventor: Bryce Nicholas Day, Townsville (AU)

( * ) Notice: Subject to any disclaimer, the term of this patent is extended or adjusted under 35 U.S.C. 154(b) by 0 days.

(21) Appl. No.: 16/952,018

(22) Filed: Nov. 18, 2020

(65) Prior Publication Data

US 2022/0151961 A1    May 19, 2022

(51) Int. Cl.
| | | |
|---|---|---|
| *A61K 31/167* | (2006.01) | |
| *A61K 31/4155* | (2006.01) | |
| *A61K 31/57* | (2006.01) | |
| *A61K 9/00* | (2006.01) | |
| *A61K 45/06* | (2006.01) | |

(52) U.S. Cl.
CPC ........ *A61K 31/167* (2013.01); *A61K 31/4155* (2013.01); *A61K 31/57* (2013.01); *A61K 9/0014* (2013.01); *A61K 9/0053* (2013.01); *A61K 45/06* (2013.01)

(58) Field of Classification Search
CPC .. A61K 31/167; A61K 31/4155; A61K 31/57; A61K 9/0014; A61K 9/0053
See application file for complete search history.

(56) References Cited

FOREIGN PATENT DOCUMENTS

| WO | 2002/000617 A2 | 1/2002 |
| WO | 2004/064747 A2 | 8/2004 |
| WO | 2009/155481 A2 | 12/2009 |

OTHER PUBLICATIONS

Student et al., European Journal of Pharmacology, 2020;866:1-13 (Year: 2020).*
International Search Report in PCT International Application No. PCT/AU2021/051361, dated Jan. 27, 2022.
Jackson, L., M., et al., "Sexual differentiation of the external genitalia and the timing of puberty in the presence of an antiandrogen in sheep", Endocrinology, Aug. 2008, vol. 149, No. 8, pp. 4200-4208.

* cited by examiner

*Primary Examiner* — San Ming R Hui
(74) *Attorney, Agent, or Firm* — Cognition IP, P.C.; Edward Steakley

(57) ABSTRACT

Provided herein are compositions, methods and kits for effectively preventing, treating, reducing, mitigating, or controlling FSIAD.

8 Claims, No Drawings

METHODS AND COMPOSITIONS FOR TREATING FEMALE SEXUAL INTEREST AND AROUSAL DISORDER

FIELD OF INVENTION

The present disclosure relates to methods, compositions and kits for treating female sexual interest and arousal disorder (FSIAD).

BACKGROUND OF INVENTION

FSIAD is defined by the Diagnostic and Statistical Manual of Mental Disorders, $5^{th}$ edition, as lack of, or significantly reduced sexual interest and/or arousal in women. A FSIAD diagnosis requires that the symptoms must cause distress to the female subject and not be accounted for by other mental disorders, drugs or medical conditions.

Sex hormones, specifically androgens, estrogens and progestins, are believed to affect female sexual interest and function. Accordingly, hormone therapies for treating FSIAD include androgen and estrogen treatments.

Androgens have been used to treat sexual dysfunction in women since the 1940's, and formulations containing testosterone have been studied extensively, including oral methyltestosterone. Although androgens improve sexual function in pre- and post-menopausal normal and FSIAD women, supra-physiological doses of androgens are more effective than physiological doses. The use of supra-physiological doses of androgens is unfortunately accompanied by serious masculinizing side effects, such as hirsutism, male pattern baldness, vocal cord thickening, clitoral enlargement, acne and breast atrophy. For this reason, supra-physiological androgen administration as a treatment for FSIAD has been abandoned for some time.

Similarly, according to some studies only supra-physiological doses of testosterone are effective in treating FSIAD and currently, there are no testosterone products that have been approved by the FDA out of long-term safety concerns, which include permanent virilization effects, increase in red blood cell (RBC) count, decrease in HDL cholesterol, and an increased risk of developing an estrogen-fueled cancer, as testosterone is converted into estrogen by the aromatase enzyme. Some clinicians prescribe "off-label" use of testosterone in form of patches, pills, gels or injections.

Estrogen helps maintain libido, maintain the vaginal epithelium and allows the vaginal lubrication response. Lowered estrogen levels following menopause are the cause of some cases of FSIAD and can successfully be treated with hormone replacement therapy (HRT). However, many cases of FSIAD in post-menopausal women are not responsive to estrogen, and HRT is not a treatment in pre-menopausal women who have adequate estrogen levels already. In addition, estrogen use, particularly in post-menopausal women, is controversial, as it can potentially increase the risk of breast, uterine and ovarian cancer as well as undesirable cardiovascular events.

Current FDA-approved treatments for FSIAD include flibanserin, a 5HT1A-receptor agonist and a 5HT2A-receptor antagonist with side effects that include low blood pressure, and bremelanotide, a melanocortin receptor agonist approved in 2019, which provides a temporary libido boost shortly after injection.

FSIAD treatments that use testosterone and are seeking FDA approval include a combination of sublingual testosterone with a PDE5 inhibitor, and a combination of sublingual testosterone with bupropion, a norepinephrine-dopamine re-uptake inhibitor, which provides a libido boost. The sublingual testosterone provides a short testosterone spike, which provides a libido boost 3.5 hours later that lasts about two hours. PDE5 inhibitors increase vaginal responses to certain sexual stimuli.

The benefit of this approach is that a short duration rise in testosterone is not likely to cause virilization. However, these drugs are not practical, as users are required to anticipate needing the drug three hours in advance of sexual activity.

More effective treatments for FSIAD are therefore needed.

SUMMARY OF INVENTION

Provided herein are compositions that can be safely administered to subjects in need thereof for effectively preventing, treating, reducing, mitigating, or controlling FSIAD. Also provided herein are methods and kits for administering the disclosed compositions.

Thus, in one embodiment, provided herein are methods for preventing, treating, reducing, mitigating, or controlling female sexual interest and arousal disorder (FSIAD). The disclosed methods comprise administering to a subject in need thereof (i) a non-steroidal anti-androgen drug having minimal blood-brain-barrier penetration in a dosage that completely or partially blocks peripheral androgen receptors; and (ii) a supra-physiological dose of an anabolic androgenic steroid (AAS), a pro-drug, precursor or pro-hormone of an AAS, or a selective androgen receptor modulator (SARM), thereby effectively preventing, treating, reducing, mitigating, or controlling FSIAD.

Additionally provided herein are compositions for preventing, treating, reducing, mitigating, or controlling FSIAD. The disclosed compositions comprise (i) a non-steroidal anti-androgen drug having minimal blood-brain-barrier penetration; and (ii) a supra-physiological dose of an anabolic androgenic steroid (AAS), a pro-drug, precursor or pro-hormone of an AAS, or a selective androgen receptor modulator (SARM).

Also provided herein are kits for preventing, treating, reducing, mitigating, or controlling FSIAD. The disclosed kits comprise: (i) darolutamide formulated as a pill, tablet, capsule, powder, bead, lozenge, dragee, or granule for oral administration with instructions to be taken twice daily; (ii) an anabolic androgenic steroid (AAS), a pro-drug, precursor or pro-hormone of the AAS, or a selective androgen receptor modulator (SARM), formulated for oral, parenteral or transdermal administration; (iii) optionally injection or patch application tools; and (iv) instructions for use.

In some embodiments, the non-steroidal anti-androgen drug having minimal blood-brain-barrier penetration, and the anabolic androgenic steroid (AAS), the pro-drug, precursor or pro-hormone of the AAS, or the selective androgen receptor modulator (SARM) are formulated into a single composition for oral administration.

In other embodiments, the non-steroidal anti-androgen drug having minimal blood-brain-barrier penetration, and the anabolic androgenic steroid (AAS), the pro-drug, precursor or pro-hormone of the AAS, or the selective androgen receptor modulator (SARM) are formulated into separate compositions.

In some embodiments, the non-steroidal anti-androgen drug having minimal blood-brain-barrier penetration is administered orally, and the anabolic androgenic steroid (AAS), or the pro-drug, precursor or pro-hormone of the AAS is administered orally, parenterally or transdermally in supra-physiological bioavailable dosages of 15-150 mg/week, and the selective androgen receptor modulator (SARM) is administered orally, parenterally or transdermally in supra-physiological bioavailable dosages of 1-100 mg/day.

The non-steroidal anti-androgen drug having minimal blood-brain-barrier penetration can be darolutamide or bicalutamide. In some embodiments, darolutamide or bicalutamide are orally administered. Darolutamide is orally administered in a dosage between 150 mg and 900 mg twice daily, with a total dosage between about 300 mg and 1800 mg/day. Bicalutamide is orally administered in a dosage between 10 and 100 mg/day.

In some embodiments, the non-steroidal anti-androgen drug having minimal blood-brain-barrier penetration is darolutamide, and the AAS is testosterone, dihydrotestosterone, mesterolone, drostanolone, metenolone, any pro-drug, precursor or pro-hormone thereof, or any combination thereof.

In other embodiments, the non-steroidal anti-androgen drug having minimal blood-brain-barrier penetration is darolutamide, and the pro-drug, precursor or pro-hormone of the AAS is dehydroepiandrosterone, epiandrosterone, any pro-drug, precursor or pro-hormone thereof, or any combination thereof.

In yet other embodiments, the non-steroidal anti-androgen drug having minimal blood-brain-barrier penetration is darolutamide, and the SARM is ostarine (MK-2866), BMS-564 929, ligandrol (LGD-4033), AC-262, 536, LGD-2226, LGD-3303, 5-40503, S-23, RAD140, any pro-drug, precursor or pro-hormone thereof, or any combination thereof.

In some embodiments, the subject is a pre-menopausal woman, and the disclosed methods may further comprise administering to the woman an oral contraceptive. Suitable oral contraceptives include, but are not limited to, a combined estrogen-progesterone formulation, a progesterone formulation, or a continuous or extended use pill.

In other embodiments, the subject is a post-menopausal woman, and the disclosed methods may further comprise administering to the woman an estrogen-progesterone formulation, an estrogen hormone replacement therapy, or an oestrogen.

The methods, compositions and kits provided herein present several attractive features and desirable properties that make them suitable for use to treat a variety of conditions associated with FSIAD in human subjects. For example, the disclosed methods, compositions and kits are extremely safe, prevent virilization side effects, and may be administered to pre-menopausal and post-menopausal women. Furthermore, the therapeutic effect is synergistically increased upon combination of darolutamide with an anabolic androgenic steroid (AAS), a pro-drug, precursor or pro-hormone of the AAS, or a selective androgen receptor modulator (SARM).

The foregoing and other features of the disclosure will become more apparent from the following detailed description of several embodiments.

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties for a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

To facilitate review of the various embodiments of this disclosure, the following explanations of specific terms are provided:

Administer or Apply: To provide or give a subject a composition, such as a pharmaceutical composition, by an effective route. Exemplary routes of include, but are not limited to, oral, topical, transdermal, muscular, mucosal, and sub-mucosal routes.

Analog: A compound having a structure similar to another, but differing from it, for example, in one or more atoms, functional groups, or substructure.

Androgen: Any natural or synthetic steroid hormone that regulates the development and maintenance of male characteristics in vertebrates by binding to androgen receptors. Androgens are synthesized in the testes, ovaries and adrenal glands, and are involved in sexual function by affecting libido and sexual arousal.

Antagonist: A molecule that, upon binding to a cell receptor, competes and/or interferes with one or more ligands binding the same receptor, and thus reduces or prevents a response elicited by those ligands.

Antibiotic: A chemical substance capable of treating bacterial infections by inhibiting the growth of, or by destroying existing colonies of bacteria and other microorganisms.

Anti-inflammatory agent: An active agent that reduces inflammation and swelling.

Antioxidant: An active agent that inhibits oxidation or reactions promoted by oxygen or peroxides.

Antiviral Agent: An active agent that inhibits the replication of or destroys viruses.

Bioassay: An analytical method to determine safety, concentration or potency of a substance by its effect on living cells or tissues. A bioassay may involve the application of a stimulus, such as a drug, to a subject, a tissue or a cell line, to determine a particular effect of the stimulus on the subject, tissue or cell line.

Blood-Brain Barrier: A highly selective semipermeable layer of endothelial cells that prevents solutes in the blood from non-selectively crossing into the extracellular fluid of the central nervous system where neurons reside.

Contacting: Placement in direct physical association; includes both in solid and liquid form. Contacting can occur in vitro with isolated cells (for example in a tissue culture dish or other vessel), ex vivo with cells or tissues isolated from an organism, or in vivo by administering an active agent to a subject.

Control: A reference standard. In some examples, a control is a known value or range of values, such as one indicative of the presence or the absence of a disease. In some examples, a control is a value or range of values, indicating a response in the absence of a therapeutic agent.

Drug or Active Agent: A chemical substance or compound that induces a desired pharmacological or physiological effect, and includes therapeutically effective, prophylactically effective, or systematically effective agents. The terms also encompass pharmaceutically acceptable, pharmacologically active derivatives and analogs of those active agents specifically mentioned herein, including, but not limited to, salts, esters, amides, prodrugs, active metabolites, inclusion complexes, analogs, and the like.

Effective amount: The amount of an active agent (alone or with one or more other active agents) sufficient to induce a desired response, such as to prevent, treat, reduce and/or ameliorate a disease or a condition. Effective amounts of an active agent, alone or with one or more other active agents, can be determined in many different ways, such as assaying for a reduction in of one or more signs or symptoms associated with the disease or condition in the subject or measuring the level of one or more molecules associated with the condition to be treated.

Inhibiting a condition: Reducing, slowing, or even stopping the development of a condition, for example, in a subject who is at risk of developing or has a particular condition.

Localized application: The application of an active agent in a particular location in the body.

Nutraceutical: A pharmaceutical-grade and standardized nutrient, dietary supplement or food additive.

Oral: Oral administration includes pills, tablets, capsules, food, beverages, drinks, soups, baked goods, syrups, oral pharmaceutical compositions, nutraceutical formulations, and the like. Liquid dosage forms for oral administration include, but are not limited to, pharmaceutically acceptable emulsions, solutions, suspensions, syrups and elixirs.

Parenteral: A type of administration that includes subcutaneous injections, intravenous, intramuscular, intrasternal injection or infusion techniques. Compositions for parenteral injection comprise pharmaceutically acceptable sterile aqueous or nonaqueous solutions, dispersions, suspensions or emulsions as well as sterile powders for reconstitution into sterile injectable solutions or dispersions prior to use.

pH Modifier: A molecule or buffer used to achieve desired pH control in a formulation.

Pharmaceutically acceptable carriers: The pharmaceutically acceptable carriers useful in this disclosure are conventional. The nature of the carrier can depend on the particular mode of administration being employed. For instance, oral applications usually include pharmaceutically and physiologically acceptable fluids such as water, physiological saline, balanced salt solutions, aqueous dextrose, glycerol or the like as a vehicle. In addition to biologically-neutral carriers, oral compositions may also contain minor amounts of non-toxic auxiliary substances, such as wetting or emulsifying agents, preservatives, and pH buffering agents and the like.

Supra-Physiological: Any dose of a chemical agent that either is or mimics a hormone, neurotransmitter, or other naturally occurring agent, that is greater or more potent than a dose equal to a naturally occurring level of the hormone, neurotransmitter, or other naturally occurring agent. Thus, by a supra-physiological dose of an androgen, such as testosterone, it is meant a dose of testosterone (or equivalent dose of another androgen) that would increase testosterone or other androgen blood levels above those found in a normal woman.

Subject: A living multi-cellular vertebrate organism. Exemplary subjects include mammals, such as humans and non-human primates, rats, mice, dogs, cats, rabbits, cows, pigs, goats, horses, and the like.

Surface or Body Surface: A surface located on the human body or within a body orifice. Thus, a "body surface" includes, by way of example, skin, teeth, skin or mucosal tissue, including the interior surface of body cavities that have a mucosal lining.

Transdermal: A route of administration by which active ingredients are delivered across the skin for systemic distribution.

Under conditions sufficient to: A phrase that is used to describe any environment that permits the desired activity.

Methods, Compositions and Kits for the Treatment of FSIAD

Androgens stimulate the androgen receptor (AR), and include anabolic androgenic steroids (AAS) and selective androgen receptor modulators (SARMs).

AAS are androgens naturally produced by pro-hormone metabolization, and synthetic derivatives of naturally produced androgens. Testosterone and its metabolite dihydrotestosterone (DHT) are the major naturally produced AAS in humans.

SARMs are synthetic androgens, which are being studied for muscle wasting disorders and osteopenia.

Androgens exert their effects in many tissues, and are responsible for masculinization effects, including stimulation of body hair growth, muscle mass increase, skin sebum production, and erythropoiesis; thickening of the vocal cords; male pattern hair loss, acne, skeletal muscle hypertrophy, and breast atrophy. Androgen deprivation in men prevents development or causes loss of masculine features. Androgen administration to women in male doses causes their body to masculinize over a period of months to years. Androgen levels are roughly 10-20 times higher in men than women. Normal female total testosterone levels are 15-70 ng/dl. Normal male total testosterone levels are 300-1000 ng/dl.

Androgens have profound effects on sexual function. In biological women receiving testosterone as part of their gender transition therapy, 71% report an increase in libido. In men undergoing castration or androgen receptor blocker therapy for prostate cancer, loss of libido is one of the most commonly reported side effects. Complete loss of libido has been noted in women who undergo ovariectomy and adrenalectomy, due to loss of the two sources of androgen production.

Although androgens increase libido in women in a dose-dependent manner, administration of androgens for the treatment of FSIAD is limited by the serious virilization side effects, which include, but are not limited to, thickening of vocal cords, clitoris enlargement, male pattern hair growth and hair loss, acne, skeletal muscle hypertrophy, breast atrophy, increased RBC count and decreased HDL.

The increased sexual desire caused by androgens is likely mediated in the central nervous system (CNS), although the peripheral nervous system (PNS) may increase or decrease sexual desire, clitoral sensitivity, and frequency of orgasm through feedback loops. For example, increased sensitivity to sexual stimuli in the PNS could increase sexual desire in the CNS.

The present application provides a solution to the aforementioned unacceptable side effects caused by androgen administration, by providing a therapy for FSIAD that comprises a combination of a non-steroidal anti-androgen drug which has minimal blood-brain-barrier penetration, with a supra-physiological dose of an anabolic androgenic steroid, a pro-drug of an anabolic androgenic steroid, or a selective androgen receptor modulator to increase sexual desire in women.

Thus, provided herein are therapeutics, methods of use and kits that are based on combinations of specific active agents that provide sustained elevation in androgen levels and libido, and at the same time block peripheral side effects, such that the disclosed therapeutic compositions and methods of use have excellent safety profiles.

Without being bound to any theories, the AAS, AAS pro-drug or SARM in high doses increases libido by acting in the brain, and since the non-steroidal anti-androgen drug does not cross the blood-brain-barrier in humans, its administration blocks only peripheral androgen receptors and does not affect androgen receptors in the brain. Thus, the blockage of peripheral androgen receptors prevents the undesirable virilization side effects that characterize AAS, AAS pro-hormone or SARM high dose monotherapies in women.

Accordingly, the disclosed methods comprise administering to a subject in need thereof compositions that comprise a non-steroidal anti-androgen drug and an anabolic androgenic steroid (AAS), a pro-drug, precursor or pro-hormone of an AAS, or a selective androgen receptor modulator (SARM), in one or more form.

Suitable non-steroidal anti-androgen drugs, which do not cross the blood brain barrier include, but are not limited to, darolutamide and bicalutamide. In some embodiments, the non-steroidal anti-androgen drug is darolutamide. Darolutamide does not cause major adverse effects. Suitable doses of darolutamide are in a range between 150 mg and 900 mg twice daily, with a total dosage between 300 mg and 1800 mg/day. Suitable doses of bicalutamide are in a range between 10 and 100 mg/day.

In some embodiments, the dosing regimen of darolutamide may target complete blockade of the peripheral androgen receptors in women in need thereof, to prevent side effects from the supra-physiological doses of androgen stimulators. For example, such a dosing regimen of darolutamide would be appropriate in women in which androgens cause virilization easily.

In other embodiments, to prevent complete blockade of androgen receptors in healthy women, which may lead to an increased risk of breast and uterine cancer, darolutamide is dosed at a lower level to achieve a partial androgen receptor (AR) blockage, and allow some androgen to bind peripherally. This dosing regimen allows androgens to play their natural role as breast and endometrial proliferation inhibitors, and increases the efficacy of the treatment for FSIAD by increasing clitoral sensitivity and frequency of orgasm.

The non-steroidal anti-androgen drug with minimal blood-brain-barrier penetration is combined with a supra-physiological dose of an anabolic androgenic steroid (AAS), a pro-drug, precursor or pro-hormone of an AAS or a selective androgen receptor modulator (SARM), which bind to androgen receptors in the central and peripheral nervous system, to effectively increase sexual desire in women and treat FSIAD.

AASs are typically derivatives of testosterone or dihydrotestosterone (DHT). Pro-drugs, precursors and pro-hormones of AASs convert to AAS once in the body, and some convert directly to testosterone and DHT. SARMs are non-steroidal drugs, which stimulate the androgen receptor.

Suitable AASs which can be combined with darolutamide as disclosed herein include, but are not limited to, testosterone and any pro-drug, precursor and pro-hormone thereof; dihydrotestosterone and any pro-drug, precursor and pro-hormone thereof; mesterolone; drostanolone; and metenolone.

Suitable pro-drugs, precursors and pro-hormones of AASs which can be combined with darolutamide as disclosed herein include, but are not limited to, testosterone precursors, such as dehydroepiandrosterone, and dihydrotestosterone precursors, such as epiandrosterone.

The AASs and pro-drugs, precursors and pro-hormones of AASs may be administered in different dosages, according to the method of administration. For example, the AASs and pro-drugs, precursors and pro-hormones of AASs may be administered in bioavailable injectable dosages of 15-150 mg/week of active compound.

In other embodiments, since, for example, mesterolone has 3% oral bioavailability, daily dosages of 71-710 mg/day of mesterolone are required to achieve a weekly bioavailable dose of 15-150 mg/week.

Furthermore, some pro-hormones have incomplete metabolization to their target molecule. For example, a testosterone precursor may have an oral bioavailability of 50%, and a conversion rate to testosterone of 50%, such that the testosterone precursor is functionally 25% bioavailable. In this case, weekly doses of 60-600 mg/week (4×) would be needed to achieve a bioavailable dose of 15-150 mg/week.

Thus, dosages should be given such that once the AAS or pro-hormone is absorbed and converted into its active molecule, the cumulative weekly dose is 15-150 mg/week.

Suitable SARMs which can be combined with darolutamide as disclosed herein include, but are not limited to, ostarine (MK-2866), BMS-564 929, ligandrol (LGD-4033), AC-262, 536, LGD-2226, LGD-3303, S-40503, S-23 and RAD140. The SARMs may be orally administered in an absolute oral dose of 1-100 mg/day.

The disclosed compositions may be combined with additional active ingredients as needed. For example, the disclosed compositions can be used in conjunction with an oral contraceptive in pre-menopausal women, to prevent darolutamide from negatively impacting the development of a male fetus. Suitable oral contraceptives that may be combined with the disclosed compositions include, but are not limited to, combined estrogen-progesterone formulations, progesterone formulations, and continuous or extended use pills. In some embodiments, to treat FSIAD in pre-menopausal women, the disclosed compositions are combined with estrogen-progesterone formulations in response to the inhibitory effect of androgens on the pituitary, and consequent reduction of luteinizing hormone (LH) and follicle-stimulating hormone (FSH) levels, leading to decreased oestrogen production within the ovaries.

In other embodiments, for example in post-menopausal women, the disclosed compositions can be used in conjunction with estrogen hormone replacement therapy, to ensure the presence of sufficient estrogen levels for normal vaginal sexual response. Oestrogen may also increase the efficacy of androgens in treating FSIAD.

The disclosed compositions may be formulated in immediate release form, sustained release form or controlled release form, and coated using compounds that accelerate or decrease the release of the active ingredient. Thus, the disclosed compositions may comprise enteric coatings, extended-release coatings, sustained-release coatings, delayed release coatings and immediate-release coatings. Methods used to coat compositions as well as the materials used to manufacture such coatings are well known in the pharmaceutical formulary art. Coating materials may include, but are not limited to, glyceryl monostearate, glyceryl distearate, polymeric substances and waxes.

In some embodiments, the disclosed compositions are administered orally, with the total daily dose divided in two for twice daily dosing. The compositions to be administered orally may comprise darolutamide and an anabolic androgenic steroid (AAS), a pro-drug, precursor or pro-hormone of an AAS or a selective androgen receptor modulator (SARM), or the compositions to be administered orally may comprise a separate composition for darolutamide and a separate composition for the anabolic androgenic steroid (AAS), the pro-drug, precursor or pro-hormone of the AAS or the selective androgen receptor modulator (SARM).

Solid dosage forms suitable for oral administration may include, but are not limited to, capsules, tablets, pills, powders, beads, lozenges, dragees, granules, aerogels, crumbles, snaps, or the like. Such solid dosage forms may include at least one pharmaceutically acceptable excipient or carrier, such as sodium citrate or dicalcium phosphate; fillers or extenders, such as starches, lactose, sucrose, glucose, mannitol, and silicic acid; binders, such as, for example, carboxymethylcellulose, alginates, gelatin, polyvinylpyrrolidone, sucrose, and acacia; humectants, such as glycerol; disintegrating agents such as agar-agar, calcium carbonate, potato or tapioca starch, alginic acid, silicates and sodium carbonate; solution retarding agents such as paraffin; absorption accelerators, such as quaternary ammonium compounds; wetting agents such as, for example, acetyl alcohol and glycerol monostearate; absorbents such as kaolin and bentonite clay; lubricants, such as talc, calcium stearate, magnesium stearate, solid polyethylene glycols, sodium lauryl sulfate, and mixtures thereof; and buffering agents.

Solid oral dosage forms may also be formulated as dietary compositions, and may comprise any ingestible preparation that contains the disclosed therapeutics mixed with a food product. The food product can be dried, cooked, boiled, lyophilized or baked, and may be in the form of breads, cookies, teas, juices, soups, cereals, salads, sandwiches, sprouts, vegetables, candies, pills, tablets, or the like.

Liquid dosage forms for oral administration may include, but are not limited to, pharmaceutically acceptable emulsions, solutions, suspensions, syrups and elixirs, and may contain inert diluents commonly used in the art. For instance, liquid formulations may contain water, polyethylene glycol ethers, or any other pharmaceutically acceptable solvents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, and dimethyl formamide; oils, such as cottonseed, groundnut, corn, germ, olive, castor, and sesame oils; glycerol, tetrahydrofurfuryl alcohol, polyethylene glycols and fatty acid esters of sorbitan; adjuvants, such as wetting agents; emulsifying and suspending agents, such as ethoxylated isostearyl alcohols, polyoxyethylene sorbitol, sorbitan esters, microcrystalline cellulose, aluminum metahydroxide, bentonite, agar-agar, tragacanth, and mixtures thereof; sweetening, flavoring, perfuming agents, and any mixture thereof.

Liquid oral dosage forms may also be formulated as dietary compositions, and may comprise any ingestible preparation that contains the disclosed therapeutics mixed with a drink product. Drink products may include, but are not limited to, teas, juices, syrups, soups, sodas, brewed drinks, fermented drinks, distilled drinks, or the like.

In some embodiments, the composition comprising darolutamide is orally administered twice daily, and the composition comprising the anabolic androgenic steroid (AAS), the pro-drug, precursor or pro-hormone of the AAS or the selective androgen receptor modulator (SARM) is administered by injection.

Parenteral administration may include subcutaneous injections, intravenous, intramuscular, intrasternal injection or infusion techniques. Suspensions for parenteral administration may be encapsulated with a variety of polymers, sugars, and chelating agents, to yield stable preparations or granules. Polymers for encapsulation may include cross-linked polymers, non-crosslinked polymers, or polymers dispersed within the crystalline structure of sugar starches or protein molecules.

Compositions for parenteral injection may comprise pharmaceutically acceptable sterile aqueous or nonaqueous solutions, dispersions, suspensions or emulsions as well as sterile powders for reconstitution into sterile injectable solutions or dispersions prior to use. Examples of suitable aqueous and nonaqueous carriers, diluents, solvents or vehicles include, but are not limited to, water, ethanol, polyols, such as glycerol, propylene glycol, polyethylene glycol, and the like, carboxymethylcellulose and suitable mixtures thereof, vegetable oils, such as olive oil, and injectable organic esters, such as ethyl oleate. Proper fluidity can be maintained, for example, by the use of coating materials such as lecithin, by the maintenance of the required particle size in the case of dispersions, and by the use of surfactants. Compositions for parenteral administration may also contain adjuvants such as, but not limited to, preservatives, wetting agents, emulsifying agents, and dispersing agents, isotonic agents, such as sugars, sodium chloride, and the like, and agents that delay absorption, such as aluminum monostearate and gelatin.

In some embodiments, the composition comprising darolutamide is orally administered twice daily, and the composition comprising the anabolic androgenic steroid (AAS), the pro-drug, precursor or pro-hormone of the AAS or the selective androgen receptor modulator (SARM) is administered topically or transdermally, either by patch or gel. The invention would come as a kit describing darolutamide to be taken twice daily and the patch or gel to be applied a certain amount at a certain frequency.

Topical compositions may be in form of powder, solution, emulsion, suspension, cream, salve, gel, or gum gel, and can be applied to the face, eyes, lips, teeth, hair, forehead, nails, hands, feet, shoulders, arms, back, or legs of a subject.

Transdermal compositions may be in form of patch, wound dressings, bandages, plasters, stents, implants, aerogels, crumbles, snaps, or hydrogel for transdermal application, and formulated for immediate release, extended release or sustained release. Various additives, known to those skilled in the art, may be included in transdermal formulations. Examples of additives include, but are not limited to, solubilizers, skin permeation enhancers, preservatives, such as anti-oxidants, moisturizers, gelling agents, buffering agents, surfactants, emulsifiers, emollients, thickening agents, stabilizers, humectants, dispersing agents and pharmaceutical carriers. Examples of moisturizers include, but are not limited to, jojoba oil and evening primrose oil. Suitable skin permeation enhancers include, but are not limited to, lower alkanols, such as methanol ethanol and 2-propanol; alkyl methyl sulfoxides, such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers, such as diethylene glycol monoethyl ether and diethylene glycol monoethyl ether oleate; polyoxy 35 castor oil, polyoxy 40 hydrogenated castor oil, polyethylene glycol (PEG), and polyethylene glycol derivatives, such as PEG-8 caprylic/capric glycerides; alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the disclosed compositions.

The disclosed compositions may also be administered by a variety of other routes, including mucosal, subcutaneous and intramuscular administration, and may comprise a variety of carriers or excipients known in the formulary art, such as non-toxic solid, semisolid or liquid filler, diluent, encapsulating material and formulation auxiliaries that are pharmaceutically acceptable.

Additionally provided herein are kits for the prevention, treatment, control, or management of FSIAD. The disclosed kits comprise a non-steroidal anti-androgen drug, such as darolutamide, an anabolic androgenic steroid (AAS), a pro-drug, precursor or pro-hormone of an AAS, or a selective androgen receptor modulator (SARM), in one or more form, and instructions for use.

Kits for oral administration may comprise darolutamide and the anabolic androgenic steroid (AAS), a pro-drug, precursor or pro-hormone of the AAS, or the selective androgen receptor modulator (SARM), in the same pill, tablet, capsule, powder, bead, lozenge, dragee, or granule. In other embodiments, the darolutamide and the anabolic androgenic steroid (AAS), a pro-drug, precursor or pro-hormone of the AAS, or the selective androgen receptor modulator (SARM) may each be separately formulated into different pills, tablets, capsules, powders, beads, lozenges, dragees, or granules, with the total daily dose divided in two for twice daily dosing.

In different embodiments, the disclosed kits comprise darolutamide formulated as a pill, tablet, capsule, powder, bead, lozenge, dragee, or granule for oral administration with instructions to be taken twice daily, and the anabolic androgenic steroid (AAS), a pro-drug, precursor or pro-hormone of the AAS, or the selective androgen receptor modulator (SARM) formulated for parenteral administration, with the necessary injection materials and instructions on how frequently it must be administered and in what volume.

For transdermal administration, the disclosed kits comprise darolutamide formulated as a pill, tablet, capsule, powder, bead, lozenge, dragee, or granule for oral administration with instructions to be taken twice daily, and the anabolic androgenic steroid (AAS), a pro-drug, precursor or pro-hormone of the AAS, or the selective androgen receptor modulator (SARM) formulated as patch or gel, with instructions on how frequently it must be administered and in what amounts.

In some embodiments, the subject is a mammal. In some embodiments, the subject is a human subject.

Example

Treatment of FSIAD

A woman diagnosed with FSIAD is administered a 30 mg testosterone enanthate injection weekly, and a dose of 450 mg of darolutamide twice daily to achieve partial (90%) AR blockage peripherally, rather than total (100%) AR blockage. With this treatment regimen, the woman receives the equivalent of 3 mg of testosterone acting peripherally (a physiological dose) and 30 mg of testosterone (a supra-physiological dose) acting within her central nervous system. After a one-month treatment, the woman reports increased sustained libido, increased clitoral sensitivity and increased frequency of orgasm.

Examination after one year of treatment reveals that the woman has decreased breast and endometrial cancer risk because of androgenic proliferation inhibition of breast and endometrial tissues.

It should be recognized that illustrated embodiments are only examples of the disclosed product and methods and should not be considered a limitation on the scope of the invention. Rather, the scope of the invention is defined by the following claims. We therefore claim as our invention all that comes within the scope and spirit of these claims.

The invention claimed is:

1. A method for preventing, treating, reducing, mitigating, or controlling female sexual interest and arousal disorder (FSIAD), wherein the method comprises:
   administering to a subject (i) a non-steroidal anti-androgen drug, wherein the non-steroidal anti-androgen drug is darolutamide; and (ii) a supra-physiological dose of an anabolic androgenic steroid (AAS), wherein the AAS is testosterone, dihydrotestosterone, mesterolone, drostanolone, metenolone, or a combination thereof, a pro-drug, precursor or pro-hormone of an AAS, wherein the pro-drug, precursor or pro-hormone of the AAS is dehydroepiandrosterone, epiandrosterone, or a combination thereof, or a selective androgen receptor modulator (SARM), wherein the SARM is ostarine, ligandrol, or a combination thereof.

2. The method of claim 1, wherein the non-steroidal anti-androgen drug, and the anabolic androgenic steroid (AAS), the pro-drug, precursor or pro-hormone of the AAS, or the selective androgen receptor modulator (SARM) are formulated into a single composition for oral administration.

3. The method of claim 1, wherein the non-steroidal anti-androgen drug, and the anabolic androgenic steroid (AAS), the pro-drug, precursor or pro-hormone of the AAS, or the selective androgen receptor modulator (SARM) are formulated into separate compositions.

4. The method of claim 3, wherein the non-steroidal anti-androgen drug is administered orally, and wherein the anabolic androgenic steroid (AAS), or the pro-drug, precursor or pro-hormone of the AAS is administered orally, parenterally or transdermally in supra-physiological bio-available dosages of 15-150 mg/week, or the selective androgen receptor modulator (SARM) is administered orally, parenterally or transdermally in supra-physiological bioavailable dosages of 1-100 mg/day.

5. The method of claim 1, wherein the darolutamide is orally administered in a dosage between 150 mg and 900 mg twice daily, with a total dosage between about 300 mg and 1800 mg/day.

6. The method of claim 5, wherein the subject is a pre-menopausal woman, and wherein the method further comprises administering to the woman an oral contraceptive.

7. The method of claim 6, wherein the oral contraceptive is a combined estrogen-progesterone formulation, a progesterone formulation, or a continuous or extended use pill.

8. The method of claim 5, wherein the subject is a post-menopausal woman, and wherein the method further comprises administering to the woman an estrogen-progesterone formulation, an estrogen hormone replacement therapy, or an oestrogen.

* * * * *